United States Patent [19]
Stuart

[11] Patent Number: 5,361,754
[45] Date of Patent: Nov. 8, 1994

[54] APPARATUS AND METHOD FOR CONNECTING A TRACHEOSTOMY TUBE TO A NECKPLATE

[75] Inventor: John M. Stuart, Lake Forest, Calif.
[73] Assignee: Mallinckrodt Medical, Inc., St. Louis, Mo.
[21] Appl. No.: 8,022
[22] Filed: Jan. 25, 1993
[51] Int. Cl.$^5$ .......................................... A61M 16/04
[52] U.S. Cl. ........................ 128/207.17; 128/DIG. 26
[58] Field of Search .................... 128/207.14, 207.15, 128/207.17, DIG. 26; 604/158

[56] References Cited

U.S. PATENT DOCUMENTS

| | | | |
|---|---|---|---|
| 953,922 | 4/1910 | Rogers | 128/207.17 |
| 1,835,757 | 12/1931 | Burchett | 128/207.17 |
| 3,461,877 | 8/1969 | Morch | 128/207.14 |
| 3,659,612 | 5/1972 | Shiley et al. | 128/207.15 |
| 3,693,624 | 9/1972 | Shiley et al. | 523/112 |
| 3,746,683 | 7/1973 | Salyer et al. | 260/33.2 |
| 3,794,041 | 2/1974 | Frei et al. | 606/108 |
| 3,810,474 | 5/1974 | Cross | 128/207.15 |
| 3,814,103 | 6/1974 | Fettel et al. | 128/207.15 |
| 4,009,720 | 3/1977 | Crandall | 128/207.15 |
| 4,030,494 | 6/1977 | Tenczar | 604/411 |
| 4,033,353 | 7/1977 | LeRosa | 128/207.15 |
| 4,052,990 | 10/1977 | Dodgson | 128/207.14 |
| 4,134,405 | 1/1979 | Smit | 606/108 |
| 4,152,017 | 5/1979 | Abramson | 285/260 |
| 4,156,067 | 5/1979 | Gould | 424/78.06 |
| 4,235,229 | 11/1980 | Ranford et al. | 128/207.17 |
| 4,282,876 | 8/1981 | Flynn | 604/280 |
| 4,315,505 | 2/1982 | Crandall et al. | 128/200.26 |
| 4,331,142 | 5/1982 | Degen | 128/207.15 |
| 4,332,245 | 6/1982 | Boone, Sr. | 128/207.17 |
| 4,574,806 | 3/1986 | McCarthy | 606/108 |
| 4,619,640 | 10/1986 | Potolsky et al. | 604/7 |
| 4,676,241 | 6/1987 | Webb et al. | 128/207.17 |
| 4,722,344 | 2/1988 | Cambron et al. | 128/658 |
| 4,755,174 | 7/1988 | Milewski et al. | 604/174 |
| 4,790,832 | 12/1988 | Lopez | 604/283 |
| 4,796,607 | 1/1989 | Allred, III et al. | 128/4 |
| 4,810,543 | 3/1989 | Gould et al. | 428/35.7 |
| 4,838,255 | 6/1989 | Lambert | 128/202.16 |
| 4,850,348 | 7/1989 | Pell et al. | 128/207.15 |
| 4,850,351 | 7/1989 | Hermann et al. | 606/7 |
| 4,869,718 | 9/1989 | Brader | 604/164 |
| 4,883,699 | 11/1989 | Aniuk et al. | 428/36.9 |
| 4,906,234 | 3/1990 | Voychehovski | 604/79 |
| 4,955,384 | 9/1990 | Taylor et al. | 128/657 |
| 4,965,112 | 10/1990 | Brinkman et al. | 428/36.91 |
| 4,969,879 | 11/1990 | Lichte | 604/283 |
| 5,003,989 | 4/1991 | Taylor et al. | 128/772 |
| 5,024,220 | 6/1991 | Holmgreen et al. | 128/207.18 |
| 5,041,100 | 8/1991 | Rowland et al. | 604/265 |
| 5,054,482 | 10/1991 | Bales | 128/207.14 |
| 5,056,515 | 10/1991 | Abel | 128/207.15 |
| 5,062,420 | 11/1991 | Levine | 128/204.18 |
| 5,067,496 | 11/1991 | Eisele | 128/207.15 |
| 5,083,561 | 1/1992 | Russo | 128/207.16 |
| 5,114,400 | 5/1992 | Lynn | 604/53 |
| 5,121,746 | 6/1992 | Skora | 128/203.12 |
| 5,184,611 | 2/1993 | Turnbull | 128/207.14 |
| 5,186,712 | 2/1993 | Kelso et al. | 604/165 |
| 5,282,463 | 2/1994 | Hammersley | 128/207.15 |

FOREIGN PATENT DOCUMENTS

| | | |
|---|---|---|
| 332065 | 9/1989 | European Pat. Off. . |
| 3339988A | 5/1985 | Germany . |
| 3821154C | 10/1989 | Germany . |
| 2098491A | 11/1982 | United Kingdom . |

OTHER PUBLICATIONS

The Lancet, Feb. 1965, vol. 1/65, p. 468, "New Inventions", Tracheostomy Adapters for Patients with Severe Respiratory Paralysis Who Depend on Intermittent Positive-Pressure Respiratioon.
The Lancet, Jun. 1961, p. 1326, "New Inventions", Modifications of the Negus Tracheotomy Tube.
Derwent Abstract 88-128961/19, Japan 3071259-A, Published Mar. 1988.
Shiley Medical Products, "Advertisement", Sep. 1970.

*Primary Examiner*—Edgar S. Burr
*Assistant Examiner*—Eric P. Raciti
*Attorney, Agent, or Firm*—David A. Hey

[57] ABSTRACT

A tracheostomy system having a neckplate, a tracheostomy tube having an end adapted for insertion into a patient's breathing passage and an end provided with a trach head for swivel connection to the neckplate and a connection mechanism for swivelly connecting the trach head to the neckplate without deformation of the trach head or neckplate and without thermal processing. The present invention also relates to a method for swivelly connecting a trach head to a neckplate without deformation of the trach head or neckplate and without thermal processing.

11 Claims, 3 Drawing Sheets

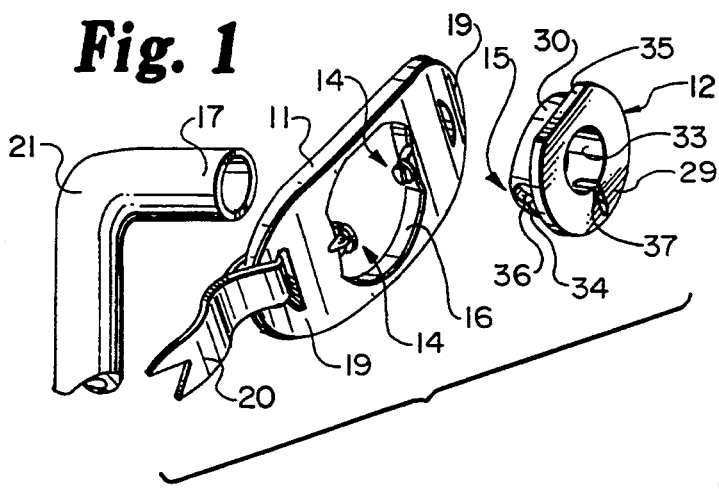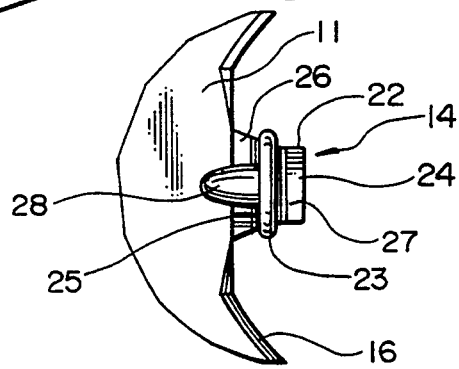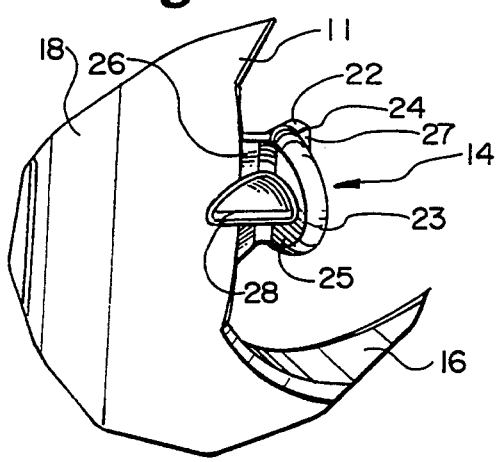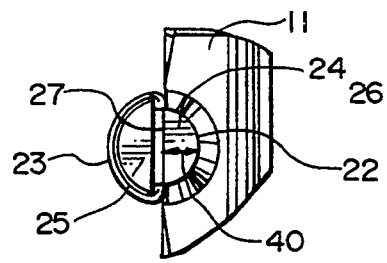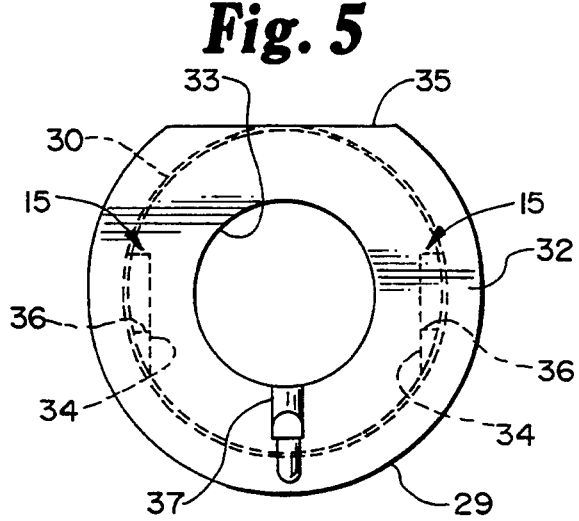

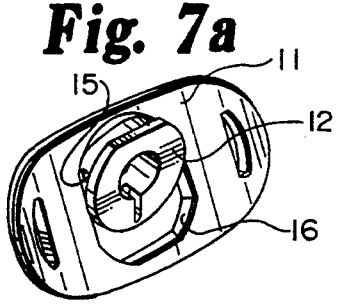
*Fig. 7a*
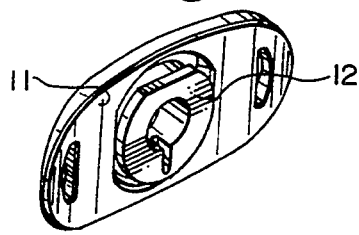
*Fig. 7b*
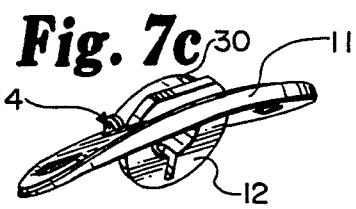
*Fig. 7c*
*Fig. 7d*
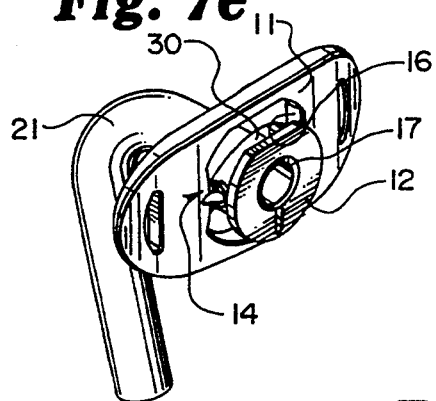
*Fig. 7e*
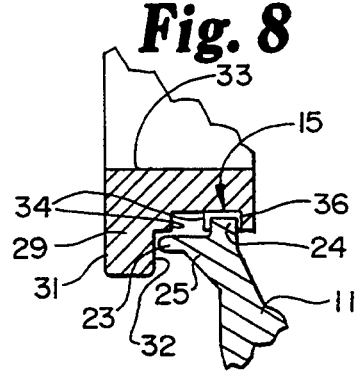
*Fig. 8*
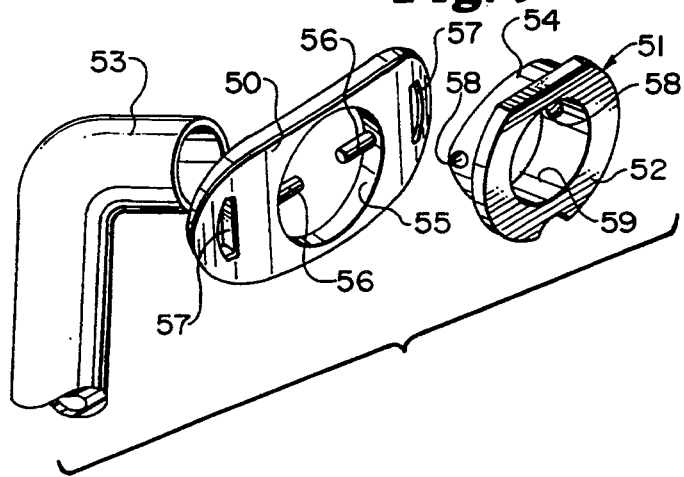
*Fig. 9*
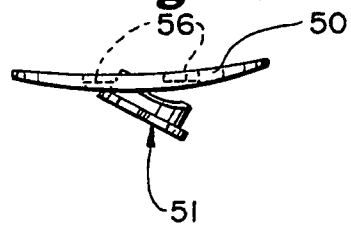
*Fig. 10a*

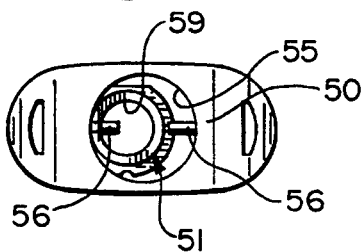
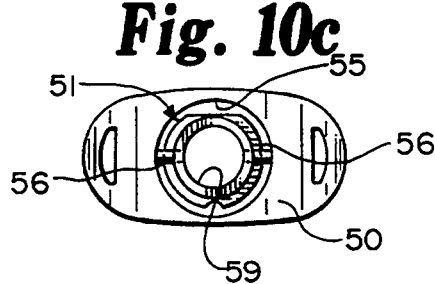
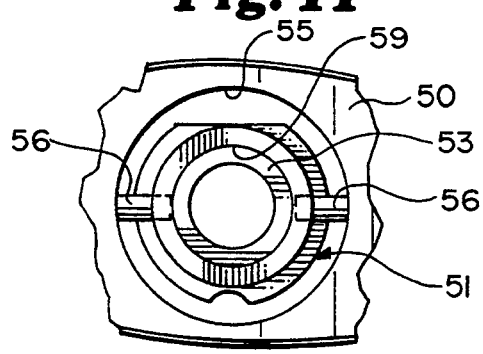
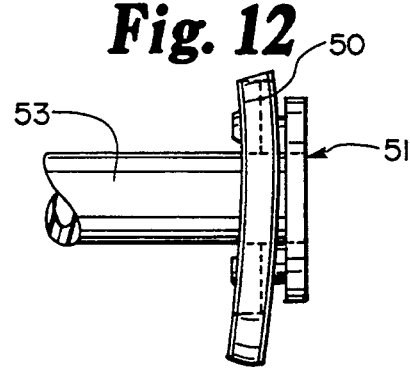
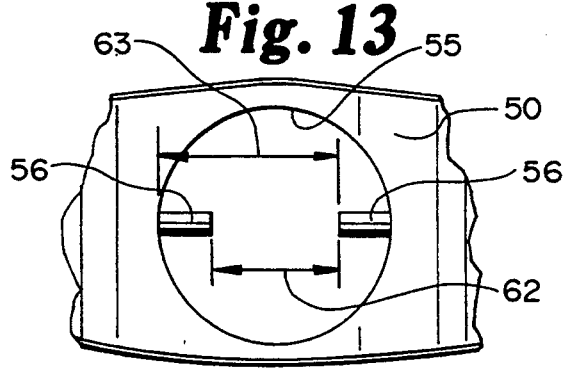
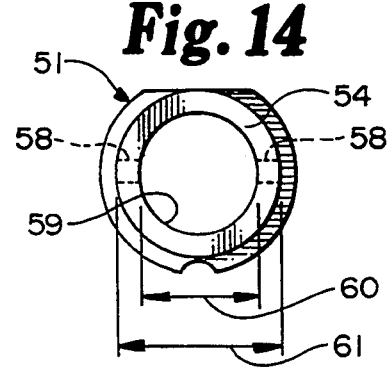

APPARATUS AND METHOD FOR CONNECTING A TRACHEOSTOMY TUBE TO A NECKPLATE

BACKGROUND OF THE INVENTION

1. Field of the Invention

The present invention relates generally to a tracheostomy device or system, and more particularly, to an apparatus and method for swivelly connecting a tracheostomy tube to the neckplate in such a device or system.

2. Summary of the Prior Art

A variety of tracheostomy devices and system exist in the prior art for providing a bypass supply of air or mixture of gases to a patient. Such devices are commonly used to bypass an obstruction in a portion of the patient's throat or breathing passage or to otherwise assist in providing oxygen to the patient's lungs. The surgical procedure involved is referred to as a tracheotomy. Typically, an incision is made in front of the patient's neck and trachea so that a tracheostomy tube can be inserted through the opening defined by the incision and into the patient's breathing passage or trachea.

A tracheostomy device or system typically includes a tracheostomy tube which extends through the opening in the patient's neck and into the trachea and a neckplate or neck engaging portion which engages the surface of the patient's neck. The proximal end of the tracheostomy tube includes a trach head for connection within an opening provided in the neckplate. Preferably such connection is a swivel connection with means being provided for swivelly connecting the trach head to pins or pivot points positioned on opposite sides of the opening in the neckplate. As used herein, the term trach head is intended to mean that portion at the proximal end of the tracheostomy tube which is connected with the neckplate.

In tracheostomy devices of the prior art, both the trach head and the neckplate are constructed from relatively rigid materials. Because of this, swivelly mounting the trach head within the opening in the neckplate has been a problem. In many prior devices, this connection is accomplished by heating or otherwise thermally processing the trach head and physically deforming the same so that the pivot holes on the trach head receive the pivot or swivel pins associated with the neckplate. After connection, the trach head is allowed to cool and resume its normal shape. Unfortunately, however, some deformity of the trach head continues to exist. This could result in an imperfect seal between these two elements which in turn can adversely affect the performance of the tracheostomy device. Further, the existing processes of swivelly connecting the trach head to the neckplate do not facilitate high speed production. Thus, such prior process are labor intensive and costly.

Accordingly, there is a need in the art for an improved tracheostomy device or system having an improved swivel connection mechanism. A further need exists for an improved apparatus and method for swivelly connecting the trach head to the neckplate in a tracheostomy device without deformation of the trach head or neckplate and without thermal processing. A still further need exists for such an apparatus and method which is cost effective and capable of high speed production.

SUMMARY OF THE INVENTION

In contrast to the prior art, the present invention relates to an improved apparatus and method for swivelly mounting a trach head relative to a neckplate in a tracheostomy device or system without deforming either the trach head or the neckplate and without thermal processing. More specifically, the apparatus of the present invention relates to a tracheostomy device for a system having a neckplate, a trach head swivelly connected to an opening in the neckplate and a tracheostomy tube adapted for insertion into the patient's breathing passage. The proximal end of the tracheostomy tube is connected to the trach head and the connected tube and trach head extend through the opening in the neckplate. The connection mechanism includes means for swivelly connecting the trach head to the neckplate without deformation of the trach head or the neckplate and without thermal processing.

Two embodiments of such apparatus are disclosed. In one embodiment, the connection means includes a pair of bearing members and a pair of corresponding bearing sockets which are connected to the neckplate and the trach head respectively. In the preferred embodiment, each of the bearing sockets is provided with an entry means in the form of a slot to receive the bearing members for seating within the bearing sockets. The entry means are positioned to receive the bearing members within a limited range of positions. Upon seating of the bearing members in the bearing sockets, the trach head is rotated to a position outside of the limited range of positions. This prevents removal of the bearing members from the bearing sockets. In this position, the tracheostomy tube is bonded to the trach head by appropriate means. Connection of the tracheostomy tube to the trach head prevents rotation of the trach head to a position in which the bearing members could be removed from the bearing sockets. This effectively provides a swivel connection without deformation of either the trach head or the neckplate and without thermal processing.

A second embodiment of the apparatus includes a neckplate with an opening and a pair of bearing pins extending inwardly from opposite sides of the opening. The pins are adapted for swivel engagement with a pair of corresponding bearing sockets or openings in the trach head. The relationship between the length of the bearing pins and the outer dimension of the trach head in the area of the bearing sockets or openings enables one of the openings to be inserted over one of the pins a sufficient distance to allow the other opening to be aligned with the other pin. The trach head is then moved toward the center so that both of the openings are supported on their respective bearing pins. The tracheostomy tube is then connected to the trach head so that it extends past a portion of the openings. This prevents lateral movement of the trach head and thus disengagement of the bearing pins from the bearing sockets.

The method aspect of the present invention relates to a method of swivelly connecting a trach head to a neckplate without deforming either the trach head or the neckplate and without thermal processing. The method involves providing a neckplate and a trach head in which one of such members includes a pair of bearing members and the other includes a pair of corresponding bearing sockets. Preferably, each of the bearing sockets has an entry means for enabling the bearing members to seat within the bearing sockets within certain limited rotational positions between the trach head and neckplate. The trach head is then positioned relative to the neckplate so that the bearing members are in the entry means. The bearing members are then moved into a seating position within the bearing sockets and the trach head is rotated relative to the neckplate about an axis of rotation to lock the bearing members within the bearing sockets and thus, the trach head relative to the neckplate. Finally, the proximal end of the tracheostomy tube is bonded to the trach head to prevent the trach head from being rotated to a position where the trach head could be removed from the neckplate.

Accordingly, it is an object of the present invention to provide a tracheostomy device or system in which the neckplate and trach head are swivelly connected to one another without deformation of either element and without thermal processing.

Another object of the present invention is to provide an apparatus for swivelly connecting the trach head and neckplate in a tracheostomy system without deformation of either the trach head or the neckplate and without thermal processing.

A further object of the present invention is to provide a swivel connection in which the trach head can be swivelly connected to the neckplate within a certain limited range and then rotated to capture the trach head relative to the neckplate and prevent removal of the same.

A further object of the present invention is to provide an improved method for swivelly connecting a trach head to a neckplate in the tracheostomy device.

A still further object of the present invention is to provide a method for swivelly connecting a trach head to a neckplate involving seating a pair of bearing members in a corresponding pair of bearing sockets, rotating the trach head at least 90 degrees to lock the trach head relative to the neckplate and then connecting the tracheostomy tube to the trach head to prevent removal of the trach head from the neckplate.

A further object of the present invention is to provide an improved apparatus and method for swivelly connecting the trach head to the neckplate which is cost effective and capable of high speed production.

These and other objects of the present invention will become apparent with reference to the drawings, the description of the preferred embodiment and method and the appended claims.

DESCRIPTION OF THE DRAWINGS

FIG. 1 is a perspective, broken apart view showing the neckplate, tracheostomy tube and trach head incorporating the swivel connection means of a first embodiment of the present invention.

FIG. 2 is an elevational, fragmentary side view of a portion of the swivel connection means of the embodiment of FIG. 1.

FIG. 3 is a perspective, fragmentary view showing a portion of the swivel connection means of the embodiment of FIG. 1.

FIG. 4 is an elevational, fragmentary end view showing a portion of the bearing member of the swivel connection of the embodiment of FIG. 1.

FIG. 5 is an elevational front view of the trach head of the embodiment of FIG. 1 with portions illustrated in broken lines.

FIG. 6 is an elevational side view of the trach head showing the bearing socket means of the swivel connection of the embodiment of FIG. 1.

FIGS. 7a–7e are perspective views of the embodiment of FIG. 1 showing the assembly sequence of swivelly connecting the trach head with the neckplate.

FIG. 8 is a sectional view as viewed along the section line 8—8 of FIG. 7d.

FIG. 9 is a perspective, broken apart view showing the neckplate, tracheostomy tube and trach head incorporating the swivel connection means of a second embodiment of the present invention.

FIG. 10a is a top elevational view of the embodiment of FIG. 9 showing the first step in the assembly sequence of swivelly connecting the trach head with the neckplate.

FIGS. 10b–10c are rear elevational views of the embodiment of FIG. 9 showing further steps in the assembly sequence of swivelly connecting the trach head with the neckplate.

FIG. 11 is a front elevational view of the embodiment of FIG. 9 showing the connection between the trach head and the proximal end of the tracheostomy tube.

FIG. 12 is an elevational top view of the embodiment of FIG. 9 showing the tracheostomy tube connected with the trach head and neckplate.

FIG. 13 is a front elevational view of the neckplate of the embodiment of FIG. 9 showing the relationship between the pin dimensions.

FIG. 14 is a rear elevational view of the trach head of the embodiment of FIG. 9 showing the relationship between the dimensions of the trach head in the area of the bearing sockets.

DESCRIPTION OF THE PREFERRED EMBODIMENT AND METHOD

The apparatus of the present invention relates generally to a tracheostomy device or system including a connection mechanism for swivelly connecting the trach head to the neckplate, or for assembling the trach head and neckplate for swivel connection, without deformation of the trach head or neckplate and without thermal processing. Two embodiments of such a mechanism are illustrated in the drawings with the first embodiment being illustrated in FIGS. 1–8 and the second embodiment being illustrated in FIGS. 9–14.

Reference is first made to FIG. 1 comprising a perspective, broken apart view of the first embodiment. Such embodiment generally includes a neckplate 11 adapted for engagement with the patient's neck, a tracheostomy tube 21 having a trach head 12 at its proximal end and a connection means for swivelly connecting the trach head 12 to the neckplate 11 without deformation of the trach head or neckplate and without thermal processing. In the embodiment of FIG. 1, the connection means comprises a bearing mechanism 14 associated with the neckplate 11 and a corresponding bearing socket means 15 comprising a bearing socket portion 36 and an entry portion 34 associated with the trach head 12.

In the preferred embodiment, the neckplate 11 is a generally elongated member having a central portion defining a center opening 16 and a pair of end portions 18. Each of the end portions 18 includes a pair of openings 19 to receive a strap 20 for connecting the neckplate 11, and thus the tracheostomy device, to the patient's neck. The opening 16 is adapted to receive the trach head 12 and tracheostomy tube 21 in the manner described below so as to provide breathing assist access to the patient's breathing passage or trachea.

A bearing support mechanism 14 is provided on opposite sides of the opening 16 and is integrally formed with the neckplate 11. As illustrated best in FIGS. 2, 3 and 4, the bearing mechanism 14 includes a bearing member 24 and a bearing cam 25. The bearing member 24 has a generally semi-circular or "D" shaped configuration defined by an external, arcuate bearing surface 22 and a relatively straight, planar side surface 27. The bearing member 24 is integrally formed with and disposed on the outer end of a support tab or member 26 which is integrally formed with the neckplate 11. With this structure, the bearing member 24 and bearing surface 22 are spaced inwardly from the edge of the opening 16. In the embodiment of FIGS. 1–8, the arcuate bearing surface 22 extends through an arc of about 180°; however, it is contemplated that the arc through which the bearing surface 22 extends could vary without deviating from the present invention. Preferably, however, the bearing surface 22 should extend through an arc of at least about 120° but no more than about 240°. Further, the present invention contemplates that the bearing surface 22 could be comprised of one or more discreet bearing points rather than a continuous bearing surface as illustrated in the preferred embodiment.

The bearing cam 25 is also integrally formed with the support tab 26 and has a generally semi-circular or "D" shaped configuration defined by the generally arcuate cam surface 23. The cam 25 is connected with the support tab 26 so that the cam surface 23 extends outwardly from the tab 26 in a direction opposite to the bearing surface 22 of the bearing member 24. Both the bearing surface 22 and the cam surface 23 have a center of curvature lying generally along the axis of rotation of the swivelly mounted trach head within the opening 16. Preferably these centers of curvature are concentric, but limited deviation from a concentric relationship is also possible in accordance with the present invention. As shown best in FIGS. 3 and 8, the bearing member 24 and the cam 25 are offset from one another along the axis of rotation with the cam 25 being closer to the edge of the opening 16. As will be described in greater detail below, this offset, together with the configuration of the member 24, enables the bearing member 24 to be inserted into the bearing socket 15 without distortion of the trach head 12 or the neckplate 11.

As illustrated best in FIGS. 2 and 3, the cam surface 23 is rounded with a constant radius. When assembled, this surface 23 functions as a flange engaging surface to assist in retaining the bearing member 24 in a seated position within the bearing socket 15. A molded brace or rib 28 is provided between the support tab 26 and the outer side of the cam 25 to provide support for the cam 25 and facilitate improved molding quality.

A mirror image of the bearing mechanism 14 is provided on the opposite side of the opening 16 of the neckplate 11 as illustrated in FIG. 1.

The trach head 12 includes a front flange 29, an integrally formed, rearwardly extending tracheostomy tube receiving portion 30 and a center opening 33. The center opening 33 extends through both the front flange 29 and the portion 30 and is adapted to receive the proximal end 17 of the tracheostomy tube 21.

As illustrated best in FIG. 6, the trach head front flange 29 includes a front or forward surface 31 and a back or rearward surface 32. The flange 29 is generally circular except for a flat portion 35 and its top. The front surface 31 includes a recessed portion 37 to facilitate connections. The portion 30 has a generally cylindrical outer configuration with a diameter less than the outer circular configuration of the flange 29. Thus, the edges of the flange 29 are spaced outwardly from the outer cylindrical surface of the portion 30. Similarly, as shown best in FIGS. 5 and 6, the rearward surface 32 of the flange 29 extends outwardly from the portion 30 to define an outer, peripheral surface portion. As will be described below, this peripheral surface portion serves as a bearing surface for the cam surface 23.

The tube receiving portion 30 is provided with a pair of bearing sockets or openings 15 on diametrically opposite sides of the portion 30. As shown best in FIG. 6, each of the bearing sockets 15 includes a generally circular bearing socket portion 36 and a portion 38 leading into or connecting with the slot or entry portion 34. Preferably the circular portion 36 has a radius of curvature approximating that, or slightly larger than that, of the bearing surface 22 (FIG. 4). This facilitates seating of the surface 22 to swivelly mount the trach head 12 to the neckplate 11. In the preferred embodiment, the circular portion 36 extends through an arc of about 225° with one end of the arc being joined with one edge of the slot 34 and the other end of the arc being joined with the other edge of the slot 34 through the portion 38.

During the swivel connection of the trach head 12 to the neckplate 11, the bearing member 24 slides along the slot 34 and into the socket 15 where, upon appropriate relative rotation between the trach head 12 and the neckplate 11, the bearing surface 22 seats in rotatable relationship within the circular portion 36. To facilitate entry of the bearing member 24 into the socket 15, the width dimension 39 of the slot 34 must be sufficiently large to permit passage of the bearing member 24. Preferably, the width 39 of the slot 34 should be slightly larger than the width dimension 40 (FIG. 4) of the member 24 to allow the member 24 to slide along the slot 34 and into the socket 15.

As shown in FIG. 5, the socket portion 36 and the entry or slot portion 34 are formed within and extend partially through the side wall of the cylindrical portion 30. As shown in FIG. 6, the slot 34 and socket portion 36 are spaced rearwardly from the rearward flange surface 32 to accommodate the cam 25 and facilitate bearing engagement between the cam surface 23 and the flange surface 32 when fully assembled.

Although both the neckplate 11 and the trach head 12 can be constructed of a variety of materials, they are generally constructed of a relatively rigid material such as polysulfone, polycarbonate or polyetherimide. Further, there is no requirement that the neckplate 11 and trach head 12 be constructed of the same material. Further, the preferred embodiment shows the beating means associated with the neckplate 11 and the bearing socket associated with the trach head 12. It is contemplated, however, that these could be reversed without deviating from the present invention.

Having described the structure of the first embodiment of the present invention, the method of connecting the trach head 12 to the neckplate 11 can be best understood by referring to the assembly sequence of FIGS. 7a–7e. Referring first to FIG. 7a, the neckplate 11 is inverted or rotated approximately 180° from the position illustrated in FIG. 1 so that the bearing mechanisms 14 are positioned on the side of the neckplate 11 away from the trach head flange 29. The trach head 12 is then placed within the center opening 16 between the bearing support mechanisms 14. In doing this, the semi-circular or "D" shaped bearing members 24 are aligned with the slot 34 extending from the bearing socket 15. In this position, the arcuate surface 22 of the member 24 faces away from the arcuate circular portion 36 of the socket 15. The trach head 12 is then slid downwardly so that bearing members 24 slide through the slots 34 and into their respective sockets 15 to the position illustrated in FIG. 7b. To accomplish this movement, the slot 34 and bearing member 24 must be appropriately aligned. In the preferred embodiment, a clearance of 10° is provided to allow for this insertion. Any orientation of the trach head 12 outside of this 10° area will not permit the member 24 to slide through the slot 34.

After the bearing members 24 are moved completely through the slot 34 so that they are positioned within the sockets 15, the neckplate 11 is rotated relative to the trach head 12 as illustrated in FIG. 7c. This rotation is continued for about 180° to the position illustrated in FIG. 7d. In this position, the bearing mechanisms 14 are on the same side of the neckplate as the front flange 29 and the bearing surfaces 22 of the bearing members 24 are seated within the circular portions 36 of the socket 15. This rotation of the neckplate 11 relative to the trach head 12 also causes the semi-circular cams 25, and in particular the cam surfaces 23, to engage the rearward surface 32 of the flange 29 as shown in FIG. 8, thereby providing a further bearing point for swivel rotation of the trach head 12 within the neckplate 11. Such rotation also captures and locks the semi-circular or "D" shaped bearing member 24 in the circular portion 36 of the bearing sockets 15.

It should be noted that the above relative rotation between the trach head 12 and the neckplate 11 is about 180°. Such arc of rotation is dictated by the particular orientation of the member 24, the socket 15 and the slot 34. Such orientation, however, should preferably be such that at least about 90° of rotation of the trach head relative to the neckplate is needed to lock such elements together in a swivel relationship.

Following this mounting of the trach head 12 to the neckplate 11, the proximal end 17 of the tracheostomy tube 21 is inserted into the opening 33 within the trach head 12 and bonded thereto by means known in the art. The distal end of the tube 21 extends outwardly from the inner surface of the neckplate 11 for insertion into the patient's breathing passage or trachea. Because of the connection of the tube 21 to the trach head 12, rotation of the neckplate 11 relative to the trach head 12 or the trach head 12 relative to the neckplate 11, beyond certain limits, is prevented. This in turn prevents the trach head 12 from being rotated to a position where it could be removed from the neckplate 11, and accordingly provides for a swivel connection without deforming either the trach head 12 or neckplate 11 and without thermal processing.

The second embodiment of the apparatus of the present invention is illustrated best in FIG. 9. Similar to the first embodiment, the embodiment of FIG. 9 includes a neckplate 50, a tracheostomy tube 53 having a trach head at its proximal end and connection means for swivelly connecting the trach head 51 relative to the neckplate 50 without distorting the trach head 51 or the neckplate 50 and without thermal processing.

The neckplate 50 includes a center opening 55 and a pair of bearing supports in the form of the bearing pins 56. The bearing pins 56 extend inwardly toward each other from diametrically opposite sides of the opening 55 and lie on a common axis. Similar to the neckplate 11 of FIG. 1, the neckplate 50 is provided with a pair of end openings 57 to facilitate connection to a patient's neck via strap means.

The trach head 51 of FIG. 9 is similar to the trach head 12 of FIG. 1 in that it includes a front flange 52 and a rearward, cylindrical tracheostomy tube receiving portion 54. The trach head 51 is provided with a centrally positioned tube receiving opening 59. A pair of bearing sockets or openings 58 are provided on diametrically opposite sides of the portion 54 to receive and mate in swivel relationship with the bearing pins 56. Preferably, the size of the openings 58 is slightly larger than the diameter of the pins 56 to accommodate assembly of the device and free swivel movement between the trach head 51 and the neckplate 50.

The assembly of the embodiment of FIGS. 9–14, and thus the method of connecting the trach head 51 to the neckplate 50 can be understood best by reference to FIGS. 10a, 10b and 10c. First, the trach head 51 is positioned relative to the neckplate 50 so that one of the bearing sockets or holes 58 is aligned with one of the bearing pins 56 as shown in FIG. 10a. The trach head 51 is then moved laterally (toward the left as viewed in FIG. 10a) until the one bearing pin 56 is fully inserted into bearing socket 58 as illustrated in FIG. 10b. In this position, one of the bearing pins 56 is fully inserted into one of the bearing sockets 58, while the other bearing pin is completely outside the other bearing socket. This permits the trach head 51, and in particular the tube receiving portion 54, to be moved so that the other bearing pin 56 is aligned with the other bearing socket 58. The trach head 51 is then moved laterally in the opposite direction to the position illustrated in FIG. 10c in which the trach head 51 is generally centrally positioned within the opening 55. This results in both of the bearing pins 56 being inserted into their corresponding bearing sockets 58 and seated therein.

Next, the proximal end of the tracheostomy of tube 53 is inserted into the interior of the center opening 59 of the trach head 51 so that its inner, proximal end extends past the pins 56. The tube 53 is then bonded to the trach head 12 by appropriate adhesive means. This connection of the tube 55 to the trach head 51 prevents lateral movement of the trach head 51 relative to the pins 56 and thus prevents the trach head 51 from being inadvertently dislodged or removed from the neckplate 50.

To facilitate the connection illustrated in FIGS. 10a–10c, 11 and 12, certain relationships must exist between the dimensions of the bearing pins 56 and the dimensions of the portion 54 in the area of the bearing sockets 58. Specifically, the dimension 62 (FIG. 13) defining the distance between the innermost ends of the pins 56 must be less than the dimension 61 (FIG. 14) defining the outer diametrical dimension of the portion 54, but preferably not less than the dimension 60 (FIG. 14) defining the inner diametrical dimension of the opening 59 in the area of the sockets 58. Further, the dimension 63 (FIG. 13) defining the length of at least one of the pins 56 plus the distance between the inner ends of the pins must not be less than the dimension 61 (FIG. 14) defining the outer diametrical dimension of the portion 54 in the area of the bearing sockets 58.

Further, to facilitate one of the pins 56 being inserted into the corresponding socket 58 as illustrated in FIG. 10a, such pin must be slightly smaller than the corresponding socket, or either a portion of such pin or its corresponding socket must be slightly elongated in cross-section to accommodate insertion of such pin into the opening at the angle illustrated in FIG. 10a.

Although the description of the present invention has been quite specific, it is contemplated that various modifications could be made to the preferred embodiment and method without deviating from the spirit of the present invention. Accordingly, it is intended that the scope of the present invention be dictated by the appended claims rather than by the description of the preferred embodiment and method.

I claim:

1. A tracheostomy device comprising:
   a neckplate having an access opening;
   a trach head swivellingly connected to said neckplate at said access opening;
   a tube adapted for insertion into a patient's breathing passage, said tube connected to said trach head; and
   connection means for swivellingly connecting said trach head to said neckplate without deformation of the trach head or neckplate and without thermal processing;
   wherein said connecting means includes a pair of bearing members and a pair of corresponding bearing sockets to receive said bearing members in seating relationship, said pair of bearing members connected with one of said neckplate or trach head and said pair of bearing sockets formed in the other of said neckplate or trach head;
   and wherein said connection means further includes a cam surface associated with each of said bearing members for engagement with a portion of the other of said trach head and neckplate when said bearing members are seated within said bearing sockets.

2. The device of claim 1 wherein said bearing members are connected with said neckplate and said bearing sockets are formed in said trach head.

3. The device of claim 1 wherein said trach head includes a tube receiving portion and a flange portion, wherein said bearing members are connected with said neckplate and said bearing sockets are formed in said tube receiving portion and wherein said cam surface engages said flange portion.

4. The device of claim 1 wherein each of said bearing sockets includes a bearing socket portion and a corresponding entry means for enabling said bearing members to seat within said bearing socket portion without deformation of said neckplate or said trach head and without thermal processing.

5. The device of claim 4 wherein said entry means includes a slot extending from said corresponding bearing socket portion.

6. The device of claim 5 wherein said slot includes a passage dimension sufficiently large to permit passage of said bearing members through said slot and into said corresponding bearing socket portion.

7. A method of swivellingly connecting a trach head to a neckplate without deformation of the trach head or neckplate and without thermal processing, the steps of said method comprising:
   providing a neckplate and a trach head wherein one of said neckplate and said trach head includes a pair of bearing members and the other includes a pair of corresponding bearing sockets, each of bearing sockets having a bearing socket portion and a corresponding entry means comprising a cam surface for enabling said bearing members to seat within said bearing socket portion for rotation about an axis of rotation;
   positioning said pair of bearing members in said entry means and moving said bearing members along said cam surface into seating position within said bearing sockets; and
   rotating said trach head about said axis of rotation at least about 90° relative to said neckplate.

8. The method of claim 7 wherein said trach head is rotated about 180°.

9. The method of claim 7 wherein said bearing members are moved into seating position within said bearing sockets by movement along a direction generally perpendicular to said axis of rotation.

10. The method of claim 7 wherein said trach head includes an opening and said method includes securing a tube in said opening following said rotation step.

11. The method of claim 10 wherein said trach head is rotated about 180°.

* * * * *